United States Patent
Jo et al.

(10) Patent No.: US 7,132,577 B2
(45) Date of Patent: Nov. 7, 2006

(54) METHOD OF INHIBITING COKE FORMATION IN ETHYLENE DICHLORIDE PYROLYSIS CRACKER

(75) Inventors: Donghyun Jo, Daejeon (KR); Jongwook Bae, Daejeon (KR); Juyoul Kim, Hwaseong (KR); Sung Won Kim, Daejeon (KR); Byungchul Oh, Daejeon (KR); Seung Back Ha, Hanam (KR)

(73) Assignee: LC Chem, Ltd. (KR)

( * ) Notice: Subject to any disclaimer, the term of this patent is extended or adjusted under 35 U.S.C. 154(b) by 0 days.

(21) Appl. No.: 11/296,891

(22) Filed: Dec. 8, 2005

(65) Prior Publication Data

US 2006/0129007 A1 Jun. 15, 2006

(30) Foreign Application Priority Data

Dec. 9, 2004 (KR) .................. 10-2004-0103655

(51) Int. Cl.
*C07C 17/00* (2006.01)
*C10G 9/12* (2006.01)

(52) U.S. Cl. ................... 570/155; 208/48 AA
(58) Field of Classification Search ........... 570/155; 208/48 AA, 44 AA
See application file for complete search history.

(56) References Cited

U.S. PATENT DOCUMENTS

| | | | |
|---|---|---|---|
| 3,896,182 A | 7/1975 | Young | 260/656 R |
| 5,358,626 A | 10/1994 | Gandman et al. | 208/48 |
| 6,228,253 B1 | 5/2001 | Gandman | 208/48 AA |
| 6,454,995 B1 | 9/2002 | Tong | 422/9 |

FOREIGN PATENT DOCUMENTS

EP  0 219 960 A  4/1987

*Primary Examiner*—J. Parsa
(74) *Attorney, Agent, or Firm*—Cantor Colburn LLP

(57) ABSTRACT

Provided is a method of inhibiting the formation of coke in an ethylene dichloride to vinyl chloride monomer pyrolysis cracker. The coke formation, which occurs during an ethylene dichloride pyrolysis reaction, is inhibited by contacting a heat-transfer surface of the cracker and a boron compound. The amount of coke generated when a coke formation-inhibiting material is used is 50% or less of that when a coke formation-inhibiting material is not used. In this case, however, the ethylene chloride conversion and the selectivity to a vinyl chloride monomer during the pyrolysis reaction are not affected. Accordingly, the efficiency of the pyrolysis cracker can be maximized.

9 Claims, No Drawings

METHOD OF INHIBITING COKE FORMATION IN ETHYLENE DICHLORIDE PYROLYSIS CRACKER

CROSS-REFERENCE TO RELATED PATENT APPLICATIONS

This application claims the benefit of Korean Patent Application No. 10-2004-0103655, filed on Dec. 9, 2004, in the Korean Intellectual Property Office, the disclosure of which is incorporated herein in its entirety by reference.

BACKGROUND OF THE INVENTION

1. Field of the Invention

The present invention relates to a method of inhibiting the formation of coke in a pyrolysis cracker, and more particularly, to a method of inhibiting the formation of coke in an ethylene dichloride to vinyl chloride monomer pyrolysis cracker.

2. Description of the Related Art

Pyrolysis crackers are typically operated at temperatures of from about 400° C. to about 600° C., at gauge pressures of from about 1.4 Mpa to about 3.0 Mpa and with a residence time from about 2 seconds to about 60 seconds. Ethylene dichloride (EDC) conversion per pass through a pyrolysis cracker is normally maintained around 50–70% with a selectivity of 96–99% to a vinyl chloride product. In this case, vinyl chloride monomer (VCM) and HCl are produced. By-products from the pyrolysis process range from the very lights, such as methane, acetylene, ethylene, and methyl chloride, to the heavies, such as carbon tetrachloride, trichloroethane and solid carbonaceous material. Solid carbonaceous material is usually referred to as coke, and coke brings about problems.

Higher conversion in the pyrolysis process is, in most cases, desired. However, increasing cracking temperature, pressure, and other conditions beyond conventional operating conditions generally lead to only a small increase in the EDC conversion at the expense of the selectivity to a vinyl chloride product. Furthermore, any outstanding increase in cracking temperature and pressure causes a drastic increase in coke formation.

Such coke formation in the pyrolysis cracker results in many problems. For example, coke formation inhibits the heat transfer to reactants in the pyrolysis cracker such that combustion energy is only partially transferred to reactants and the rest of the combustion energy is lost to the surroundings. Therefore, the pyrolysis cracker is required to be heated at a higher temperature to maintain the energy in the cracker at a sufficient level. Such heating requires more fuel and the lifetime of the alloy of the cracker is reduced. Conventionally, high temperatures cause erosion or corrosion of the walls of a cracker.

Meanwhile, the coke formed in the cracker reduces the width of the reaction path of EDC, thereby causing the pressure to drop with more depth when EDC passes through the cracker. As a result, more energy is required to compress the stream of a product, such as VC, in a downstream of the process. In addition, the coke reduces the effective inner volume of the cracker, which decreases the yield of the product and affects the selectivity of the reaction. Accordingly, more EDC is required to attain VC having a desired amount.

The coke formation also causes fouling of a heat exchanger and a transfer line exchanger (TLE.) A heat exchanger and a TLE remove as much thermal energy as possible from high-temperature products to stop any product degradation. However, when coke is formed in the heat exchanger and the TLE, heat transfer is inhibited. As a result, in the TLE, an increase of the pressure of gas existing in other transfer lines decreases, and in the heat exchanger, a decrease of pressure of a product stream more increases.

Accordingly, coke is periodically removed. Known methods for the removal of coke from pyrolysis crackers include controlled combustion or mechanical cleaning, or a combination of both methods. In the combustion process, a mixture of steam air of various steam/air ratios is admitted in the pyrolysis furnace at an elevated temperature, and the coke in the cracker is burnt out under a controlled condition. This process is conventionally referred to as hot decoke. For the mechanical cleaning, coke is physically chipped off the pyrolysis cracker inner surface and removed from the cracker. Both cracking and the hot decoke operations expose the pyrolysis cracker to a cycle between a HCl and chlorinated hydrocarbon-rich reducing environment and an oxygen-rich oxidizing environment at elevated temperatures, which causes corrosion and degradation of the pyrolysis cracker and shortens the cracker time.

The pyrolysis cracker is periodically decoked every 6 to 12 months, according to purity of reactant EDC and operating conditions, such as reaction temperature, reaction pressure, a feed speed of EDC, and a cracking depth. In particular, when a heat exchanger is installed in a high-temperature EDC pyrolysis cracker to efficiently use the energy at a cracker outlet, formation of a coke precursor results in a dramatic drop of a temperature in the cracker and thus coke is more quickly deposited on the inner walls of the heat exchanger, thereby shortening the removal cycle.

Conventional methods of inhibiting coke formation will now be described.

U.S. Pat. No. 6,228,253 teaches a method of coating Groups 1A and 2A metal salts on the inner walls of a cracker tube to inhibit coke formation. This method is advantageous in that there is no need to stop the process to remove the coke. However, this method can only be used for a conventional hydrocarbon pyrolysis reaction.

U.S. Pat. No. 3,896,182 teaches a method of inhibiting coke formation by lowering the oxygen content in the EDC feed.

U.S. Pat. No. 6,454,995 teaches a method of applying a phosphine-based compound (tributyl phosphine, triphenyl phosphine, or the like) to an EDC pyrolysis cracker. This method is not so effective on inhibiting coke formation and low reproducibility. In addition, since phoshpine-based compounds are expensive, the method is not cost effective.

Coke formation in pylolysis crackers continues to be undesirable and thus effective alternative methods to more efficiently inhibit the formation of coke during a pyrolysis process are always required.

SUMMARY OF THE INVENTION

The present invention provides a method of efficiently inhibiting the formation of coke at the heat-transfer surface of an ethylene dichloride (EDC) pyrolysis cracker.

The present invention also provides a coating film that efficiently inhibits coke formation in a cracker for a long period.

The present invention also provides an efficient EDC pyrolysis cracker in which coke formation is inhibited.

According to an aspect of the present invention, there is provided a method of inhibiting the formation of coke at a heat-transfer surface of a pyrolysis cracker during an ethylene dichloride pyrolysis reaction, the method comprising contacting the heat-transfer surface and a boron compound represented by Formula 1:

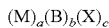
[Formula 1]

where M is a Groups IA or IIA metal, or hydrogen;
B is boron;
a and c are each independently an integer of 0–12 where $3 \leq a+c < 24$;
b is an integer of 1–10;
when a=0, X is oxygen, hydrogen, halogen, hydroxy, alkoxy, aryloxy, alkyl, aryl, alkylaryl, or arylalkyl; and
when $a \geq 1$, X is oxygen.

According to another aspect of the present invention, there is provided a coating film on an ethylene dichloride pyrolysis cracker, which is formed by, for example, spraying.

According to yet another aspect of the present invention, there is provided an ethylene dichloride pyrolysis cracker including the coating film.

According to the method, coke formation in an ethylene dichloride pyrolysis cracker is effectively inhibited and the ethylene dichloride conversion can be additionally increased. As a result, the decoking cycle of the cracker can be increased 2 times or greater and the production efficiency of a vinyl chloride monomer can be increased. In addition, the coke formation-inhibiting material has a great practical value because it can be collected for re-use and is inexpensive.

DETAILED DESCRIPTION OF THE INVENTION

Hereinafter, the present invention will be described in detail by explaining embodiments of the present invention.

Inventors of the present invention discovered that when a coating film containing a boron-based compound is applied in an ethylene dichloride (EDC) pyrolysis cracker, coke formation is effectively inhibited.

A method of inhibiting the formation of coke at the heat-transfer surface of an EDC pyrolysis cracker according to an embodiment of the present invention includes contacting the heat-transfer surface of the cracker and a boron compound represented by Formula 1:

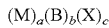
Formula 1 where M is a Group IA or IIA metal, or hydrogen;
B is boron;
a and c are each independently an integer of 0–12 where $3 \leq a+c < 24$;
b is an integer of 1–10;
when a=0, X is oxygen, hydrogen, halogen, hydroxy, alkoxy, aryloxy, alkyl, aryl, alkylaryl, or arylalkyl; and
when $a \geq 1$, X is oxygen.

In Formula 1, halogen is F, Cl, Br or I; alkyl is a C1–C20 saturated hydrocarbon; aryl is a C6–C20 aromatic mono-ring or multiple-ring system radical; alkylaryl, such as a methyl phenyl group, is an aryl having at least one alkyl substituent; arylalkyl, such as a benzyl group, is alkyl having at least one aryl substituent; alkoxy is a C1–C20 saturated hydrocarbon having an oxygen directly connected to boron; and aryloxy is a C6–C20 aromatic mono-ring or multiple-ring system radical having an oxygen atom directly connected to boron.

According to an embodiment of the present invention, the contacting of a boron compound and a cracker is realized by adding a predetermined amount of the boron compound to EDC that is to be added to a cracker. This method is not cost effective because the boron compound is required to be continuously added. In this case, however, there is no need to stop the cracker and the amount of the boron compound can be easily controlled.

In this method, boron can be used in a form of a pure compound, or mixed with a solvent, a conversion booster, or a mixture of a solvent and a conversion booster. A conversion booster that is used for a reaction through which a solvent for boron and EDC are converted into VCM is publicized in related chemical industries.

In this case, all kinds of boron compounds can be used. For example, the boron compound may be a boron halide-based compound, which may homogeneously contact the inside of the cracker due to its high solubility with respect to EDC. Examples of the boron compound include $BF_3$, $BCl_3$, $BBr_3$, and $BI_3$. Preferably, the boron compound is $BCl_3$ or $BBr_3$. By using $BCl_3$ or $BBr_3$, a high quality vinyl chloride monomer can be attained. That is, a vinyl chloride monomer obtained by using $BCl_3$ and $BBr_3$ hardly affect the final quality of PVC when PVC is synthesized. Meanwhile, the boron compound can be a borane-based compound/complex, such as $BH_3$—$NH_3$(borane-ammonia complex), $(CH_3)_3CNH_2$—$BH_3$ (tert-butylaminoborane), $(CH_3)_2CNH$—$BH_3$ (borane-dimethylamine complex), $(CH_3)_3CN$—$BH_3$ (borane-trimethylamine complex), $(C_2H_5)_3CN$—$BH_3$ (borane-triethylamine complex), $(CH_3)_2S$—$BH_3$ (borane-methyl sulfide complex), or the like. In this case, however, the inhibition effect on coke formation is smaller than that when the boron halide-based compound is used. These compounds can be used alone or at least one of these compounds can be used in a combination.

The amount of the boron compound to be added to EDC may be in the range of about 50–3000 ppm based on the weight of EDC. When the amount of the boron compound is less than 50 ppm, the inhibition effect on the coke formation is small. When the amount of the boron compound is greater than 3000 ppm, the pyrolysis process becomes expensive due to excessive use of the boron compound and by-products increase.

The location where the boron compound is added to the EDC is not limited. For example, the boron compound can be added to the EDC before the EDC is added to the pyrolysis cracker.

According to another embodiment of the present invention, a boron compound having high solubility with respect to water is applied to a heat-transfer surface of a pyrolysis cracker, after a periodic removal process of the pyrolysis cracker, and before the EDC is added to the pyrolysis cracker. In this case, at least one method selected from the group consisting of a spraying method, an impregnating method, a painting method, an electric plating method, a physical vapor deposition method, and a chemical vapor deposition method can be used.

According to the current embodiment of the present invention, all kinds of boron compounds can be used. For example, the boron compound can be $H_3BO_3$; $B_2O_3$; a boron halide-based compound, such as $BF_3$, $BCl_3$, $BBr_3$, or $BI_3$; or a borate-based compound, such as sodium perborate ($BNaO_3$), barium metaborate monohydrate ($B_2BaO_4$), potassium tetraborate tetrahydrate ($B_4K_2O_7$), or $B_4Li_2O_7$ (lithium tetraborate).

In all the methods of inhibiting coke formation described above, a phosphorous compound represented by Formula 2, in addition to the boron compound, can be further added:

$$(P)_a(R)_b \qquad \text{Formula 2}$$

where P is phosphorus;
a is an integer of 1–10;
b is an integer of 3–10; and
R is oxygen, halogen, hydroxy, alkoxy, aryloxy, alkyl, aryl, alkylaryl, or arylalkyl.

In the mixture of the boron compound and the phosphorous compound, the amount of the phosphorous compound may be in the range of 1–99% by weight, and preferably, 5–50% by weight. When the amount of the phosphorous compound is outside this range, the inhibition effect on the coke formation is small, which is identified in Comparative Examples 1 through 4 and by Table 1.

When a boron compound having high solubility with respect to water is applied to a heat-transfer surface of a pyrolysis cracker, after a periodic removal process of the pyrolysis cracker, and before the EDC is added to the pyrolysis cracker, the boron compound is coated on an inner surface of the cracker. In this case, the boron compound is deposited in the cracker at high temperature, and thus, the boron compound can exist in other forms different from a liquid state. For example, the boron compound may exist in a form of a hydrate, oxide, pyrolysis product, oligomer, or sintered product thereof. Ultimately, the boron compound may exist in a glassy state or an enamel state. In addition, even in this case, the phosphorus compound represented by Formula 2, in addition to the boron compound, may be further contained in the coating film.

The present invention will be described in further detail with reference to the following examples. These examples are for illustrative purposes only and are not intended to limit the scope of the present invention.

COMPARATIVE EXAMPLE 1

A pyrolysis reaction was performed using 99.7% EDC (containing 1600 ppm of $CCl_4$), in a 0.5-inch SUS-316 cracker having a length of 50 cm, for 20 hours, at a maximum temperature of 500° C., with a residence time of 40 sec. The amount of coke generated and the EDC conversion were measured.

COMPARATIVE EXAMPLE 2

A pyrolysis reaction was performed using a mixture of EDC and 200 ppm of tributyl phosphine based on weight in a 0.5-inch SUS-316 cracker having a length of 50 cm, for 20 hours, at a maximum temperature of 500° C., with a residence time of 40 sec. The amount of coke generated and the EDC conversion were measured.

COMPARATIVE EXAMPLE 3

Under the same conditions as in Comparative Example 2, EDC was mixed with 50 ppm of $PCl_3$, and a pyrolysis reaction was performed for 20 hours. The amount of coke generated and the EDC conversion were measured.

COMPARATIVE EXAMPLE 4

Under the same conditions as in Comparative Example 2, EDC was mixed with 200 ppm of $PCl_3$, and a pyrolysis reaction was performed for 20 hours. The amount of coke generated and the EDC conversion were measured.

TABLE 1

|  | Relative amounts of the coke generated (%) | EDC conversion (%) | By products (In EDC) |
| --- | --- | --- | --- |
| Comparative Example 1 | 100 | 75 | 2.5% |
| Comparative Example 2 | 110 | 75 | 2.6% |
| Comparative Example 3 | 90 | 76 | 2.6% |
| Comparative Example 4 | 75 | 77 | 2.7% |

In Comparative Examples 1 through 4, when a phosphine compound was added, the amount of coke generated decreased by as little a maximum of 25%, or rather, increased by 110%. Therefore, it was found that the addition of a phosphine compound resulted in a very small effect or low reproducibility.

COMPARATIVE EXAMPLE 5

A pyrolysis reaction was performed using 99.9% EDC in a 1-inch SUS-316 cracker having a length of 60 cm, for 20 hours, at the maximum temperature of 550° C., with the residence time of 40 sec. The amount of coke generated and the EDC conversion were measured.

EXAMPLE 1

A pyrolysis reaction was performed using the mixture of EDC and 500 ppm of $BBr_3$ based on weight in a 1-inch SUS-316 cracker having a length of 60 cm, for 20 hours, at a maximum temperature of 550° C., with the residence time of 40 sec. The amount of coke generated and the EDC conversion were measured.

EXAMPLE 2

Under the same conditions as in Example 1, EDC was mixed with 300 ppm of $BCl_3$, and a pyrolysis reaction was performed for 20 hours. The amount of coke generated and the EDC conversion were measured.

TABLE 2

|  | Relative amounts of the coke generated (%) | EDC conversion (%) | By products (In EDC) |
| --- | --- | --- | --- |
| Comparative Example 5 | 100 | 79 | 3.5% |
| Example 1 | 45 | 82 | 3.6% |
| Example 2 | 50 | 82 | 3.6% |

In Table 2, the amount of coke generated according to Comparative Example 5 where a boron compound was not added and the amounts of coke generated according to Examples 1 and 2 where 500 ppm and 300 ppm of the boron compound were added, respectively, are shown. When a pyrolysis reaction was performed after the cracker was treated with a coke formation-inhibiting material according to an embodiment of the present invention, the amount of coke generated was decreased by as much as 55% of that in Comparative Example 5. Furthermore, the EDC conversion was increased and the selectivity to a VCD that was a final product was not affected. From these results, it was assumed that the formation of a coke precursor and $FeCl_3$ that is known as a coke formation-inducing material on the surface of a cracker tube was inhibited by the treatment with the coke formation-inhibiting material, and the boron compound inhibited the conversion from the coke precursor into coke.

As described above, according to an embodiment of the present invention, these methods are effective to inhibit coke formation during EDC pyrolysis. When a coke formation-inhibiting material was used, the amount of coke generated was decreased by 50% or greater than the amount of coke generated when a coke formation-inhibiting material is not used. In addition, since the coke formation-inhibiting material does not affect the EDC conversion and the selectivity to a vinyl chloride monomer, the efficiency of the pyrolysis cracker can be maximized. In addition, the decoking cycle of the EDC pyrolysis cracker can be increased 2 times or greater, and thus, additional VCM can be produced. The coke formation-inhibiting material can be collected for re-use, and is inexpensive.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of inhibiting the formation of coke at a heat-transfer surface of a pyrolysis cracker during an ethylene dichloride pyrolysis reaction, the method comprising contacting the heat-transfer surface and a boron compound represented by Formula 1:

$$(M)_a(B)_b(X)_c \quad \text{Formula 1}$$

where M is a Groups IA or IIA metal, or hydrogen;
B is boron;
a and c are each independently an integer of 0–12 where $3 \leq a+c < 24$;
b is an integer of 1–10;
when a=0, X is oxygen, hydrogen, halogen, hydroxy, alkoxy, aryloxy, alkyl, aryl, alkylaryl, or arylalkyl; and
when $a \geq 1$, X is oxygen.

2. The method of claim 1, wherein the boron compound is added to an ethylene dichloride that is to be put into the pyrolysis cracker.

3. The method of claim 2, wherein the boron compound comprises at least one compound selected from the group consisting of $BF_3$, $BCl_3$, $BBr_3$, $BI_3$, $BH_{13}$—$NH_3$, $(CH_3)_3CNH_2$—$BH_3$, $(CH_3)_2CNH$—$BH_3$, $(CH_3)_3CN$—$BH_3$, $(C_2H_5)_3CN$—$BH_3$ and $(CH_3)_2S$—$BH_3$.

4. The method of claim 2, wherein the amount of the boron compound that is to be added to the ethylene dichloride is in the range of 50–3000 ppm based on the weight of the ethylene dichloride.

5. The method of claim 1, wherein the boron compound is applied to the heat-transfer surface of the pyrolysis cracker before the ethylene dichloride is added to the pyrolysis cracker.

6. The method of claim 5, wherein the application of the boron compound may be performed using at least one method selected from the group consisting of a spraying method, an impregnating method, a painting method, an electric plating method, a physical vapor deposition method, and a chemical vapor deposition method.

7. The method of claim 5, wherein the boron compound comprises at least one compound selected from the group consisting of $H_3BO_3$, $B_2O_3$, $BF_3$, $BCl_3$, $BBr_3$, $BI_3$, $BNaO_3$, $B_2BaO_4$, $B_4K_2O_7$ and $B_4Li_2O_7$.

8. The method of claim 1, wherein a phosphorus compound represented by Formula 2 is further added to the boron compound:

$$(P)_a(R)_b \quad \text{Formula 2}$$

where P is phosphorus;
a is an integer of 1–10;
b is an integer of 3–10; and
R is oxygen, halogen, hydroxy, alkoxy, aryloxy, alkyl, aryl, alkylaryl, or arylalkyl.

9. The method of claim 8, wherein an amount of the phosphorus compound is in the range of 5–50 % by weight based on the weight of the mixture of the boron compound and the phosphorus compound.

* * * * *